(12) United States Patent
Belford et al.

(10) Patent No.: US 7,550,717 B1
(45) Date of Patent: Jun. 23, 2009

(54) QUADRUPOLE FAIMS APPARATUS

(75) Inventors: Michael W. Belford, Santa Clara, CA (US); Jean Jacques Dunyach, San Jose, CA (US); Randy W. Purves, Orleans (CA)

(73) Assignee: Thermo Finnigan LLC, San Jose, CA (US)

( * ) Notice: Subject to any disclaimer, the term of this patent is extended or adjusted under 35 U.S.C. 154(b) by 213 days.

(21) Appl. No.: 11/607,789

(22) Filed: Nov. 30, 2006

(51) Int. Cl.
- B01D 59/44 (2006.01)
- H01J 49/00 (2006.01)
- H01J 49/28 (2006.01)

(52) U.S. Cl. .............. 250/281; 250/290; 250/292; 250/293; 250/294

(58) Field of Classification Search .......... 250/281, 250/290, 292, 293; 96/15, 25, 54, 75, 86, 96/87, 88
See application file for complete search history.

(56) References Cited

U.S. PATENT DOCUMENTS

| | | | |
|---|---|---|---|
| 3,621,240 A | 11/1971 | Cohen et al. | |
| 3,648,046 A | 3/1972 | Denison et al. | |
| 3,925,663 A | 12/1975 | Hiller et al. | |
| 4,704,532 A * | 11/1987 | Hua | 250/292 |
| 5,439,513 A * | 8/1995 | Periasamy et al. | 96/25 |
| 6,441,370 B1 | 8/2002 | Khosla et al. | |
| 6,713,758 B2 | 3/2004 | Guevremont et al. | |
| 6,730,904 B1 | 5/2004 | Wells | |
| 6,784,424 B1 * | 8/2004 | Willoughby et al. | 250/292 |
| 6,806,463 B2 * | 10/2004 | Miller et al. | 250/286 |
| 6,822,224 B2 | 11/2004 | Guevremont | |
| 7,034,292 B1 * | 4/2006 | Whitehouse et al. | 250/289 |
| 7,075,070 B2 | 7/2006 | Lee et al. | |
| 7,339,164 B2 * | 3/2008 | Miller et al. | 250/282 |
| 2003/0150985 A1 * | 8/2003 | Guevremont et al. | 250/287 |
| 2006/0027746 A1 * | 2/2006 | Guevremont et al. | 250/292 |
| 2006/0038121 A1 * | 2/2006 | Guevremont | 250/290 |
| 2007/0023635 A1 * | 2/2007 | Bateman et al. | 250/282 |
| 2008/0067350 A1 * | 3/2008 | Li | 250/287 |

FOREIGN PATENT DOCUMENTS

WO WO2004030129 * 8/2004

* cited by examiner

Primary Examiner—Jack I Berman
Assistant Examiner—Brooke Purinton
(74) Attorney, Agent, or Firm—Freedman & Associates; Charles B. Katz

(57) ABSTRACT

A combined rf-only/FAIMS analyzer is disclosed for use in mass spectrometry and other applications. The disclosed apparatus includes a plurality of flat-plate electrodes arranged around a longitudinal axis of the apparatus so as to define generally a parallelogram in a cross section taken in a plane that is normal to the longitudinal axis. FAIMS is removed electronically when not desired by application of radio frequency (rf) waveforms to the flat-plate electrodes.

10 Claims, 4 Drawing Sheets

QUADRUPOLE FAIMS APPARATUS

FIELD OF THE INVENTION

The instant invention relates generally to High Field Asymmetric Waveform Ion Mobility Spectrometry (FAIMS), and more particularly to a quadrupole FAIMS apparatus.

BACKGROUND OF THE INVENTION

High Field Asymmetric Waveform Ion Mobility Spectrometry (FAIMS) is a technology that is capable of separating gas-phase ions at atmospheric pressure. In FAIMS, the ions are introduced into an analyzer region across which a radio frequency (rf) waveform, the magnitude of which is referred to as dispersion voltage (DV), is applied such that the ions are alternately subjected to high and low electric fields. The waveform is asymmetric; for example, the high field may be applied for one time unit followed by an opposite-polarity low field of half of the high field component applied for twice as long. The field-dependent change in the mobility of the ions causes the ions to drift towards the walls of the analyzer region. Since the dependence of ion mobility on electric field strength is compound specific, this leads to a separation of the different types of ions one from the other, and is referred to as the FAIMS separation or the FAIMS mechanism. In order to transmit an ion of interest through FAIMS, an appropriate direct current compensation voltage (CV) is applied to compensate for the drift of the ion of interest toward the analyzer wall. By varying the CV, different ions are selectably transmitted through the FAIMS device.

In addition to its unique gas-phase ion separation mechanism, an atmospheric pressure ion focusing mechanism also exists when using FAIMS, resulting in high ion transmission. When used with mass spectrometry (MS) and tandem liquid chromatography mass spectrometry (LC-MS), FAIMS provides an extra degree of selectivity without introducing prohibitively large drops in signal intensity, compared with the signal intensity without FAIMS being present. This selectivity is especially important for analyses where several interferences may be present, e.g., in biological samples.

Although there are many instances where FAIMS is used beneficially to improve the selectivity of an analytical method, there also are certain cases where the use of FAIMS is not desirable. Examples include cases where (1) the background of an assay is already very low, and (2) FAIMS is not compatible with the time scale of the analysis. In the first example, FAIMS may be left in operational mode as long as it does not degrade the analysis. However, this may not be desirable when using an established method since additional method development work would need to be done and the new method with FAIMS in operational mode would require validation. The second example is more problematic because FAIMS negatively impacts the analysis. This occurs because typical residence times for ions to pass through a FAIMS device operating at atmospheric pressure in a commercial instrument environment are in the tens of milliseconds range. Consider the case of analyses in which twenty analyte compounds are injected into a column and are subsequently eluted from the column during a finite period of time, typically 2-20 seconds although the actual time may be shorter or longer. Several points for each analyte compound are required to properly define the peak shape, in order to determine the amount of each analyte compound in the sample. When FAIMS is not present, the MS can be set to detect each analyte compound for 10 ms in a looped detection sequence such that a sampling of the amount of all twenty analyte compounds is obtained every 200 ms. For a chromatographic peak width of 2 s, this enables 10 points to be sampled per analyte compound. The situation is quite different when a FAIMS device is present with a 100 ms ion residence time and in which each analyte compound is transmitted at a different CV value. After detecting one analyte compound for 10 ms, the CV must then be changed which is followed by a delay of 100 ms before the next compound passes through the FAIMS to the MS. Accordingly, with FAIMS present it takes 2.2 s to sample just one point for each one of the twenty analyte compounds. Under these conditions, it is possible to miss the elution of an analyte compound entirely, and in any event, too few points are sampled to properly reconstruct the chromatographic peak shapes. As a consequence, for analyses of this type, the use of FAIMS is not desirable.

The need to physically remove the FAIMS hardware each time the use of FAIMS is not desired (typically requiring the same amount of time and effort as changing an ion source) presents a serious impediment to the routine usage of FAIMS. Ideally, the change is achieved either electronically or in the software that operates the system, without physically removing the FAIMS hardware.

In U.S. Pat. No. 6,824,224 filed on Mar. 14, 2001, the entire contents of which is incorporated herein by reference, Guevremont discloses a FAIMS analyzer that is built in the same physical configuration as a quadrupole mass filter analyzer. The quadrupole FAIMS is described for separating isobaric ions, e.g. ions having the same mass-to-charge ratio, which are produced in a collision cell that is disposed immediately in front of the quadrupole FAIMS. When isobaric ions are not produced in the collision cell, and thus ion separation using FAIMS is not required, the quadrupole FAIMS is operated in rf-only mode and its separation function is effectively removed from the system.

In United States Publication 2006/0038121 filed on Sep. 23, 2003, the entire contents of which is incorporated herein by reference, Guevremont discloses a combined rf-only and FAIMS quadrupole cell. In one embodiment the combined rf-only and FAIMS quadrupole cell is disposed directly behind the entrance orifice of the mass spectrometer. The cell is operated alternately in FAIMS separation mode and rf-only mode so as to effect a FAIMS separation and then subsequently focus the remaining ions toward the longitudinal axis for introduction into a detector.

Certainly, a FAIMS analyzer that is based on the same physical configuration as a quadrupole mass filter analyzer does support removal of the FAIMS separation component of an ion analysis path, without physically removing any components of the system. That being said, the ion transmission efficiency that is achievable with the FAIMS "turned off" is lower than the expected ion transmission efficiency when the FAIMS hardware is not present. This is due, at least in part, to a noding effect resulting from the periodic nature of ion motion through a quadrupole and the efficiency of transferring ions through the quadrupole exit lens. In addition to reduced ion transmission efficiency, a FAIMS analyzer based on the same physical configuration as a quadrupole mass analyzer requires a set of precision-machined rods that are rigidly supported in a precise, spaced relationship. Accordingly, the manufacture of this type of FAIMS device is highly specialized and is relatively expensive.

There exists a need for a FAIMS apparatus that overcomes at least some of the above-mentioned limitations.

SUMMARY OF EMBODIMENTS OF THE INVENTION

According to an aspect of the instant invention there is provided an apparatus for transmitting ions in the gas phase, the apparatus selectably switchable between a first operating mode for transmitting ions with separation according to the FAIMS principle and a second operating mode for transmitting ions using the principle of an rf-only ion guide device, the apparatus comprising: an analyzer assembly comprising an analytical gap defined by a space that is bounded by at least four electrode surfaces, the at least four electrode surfaces arranged around a longitudinal axis that extends along a first direction through the analytical gap, the at least four electrode surfaces comprising: a first electrode surface and a second electrode surface, the second electrode surface disposed in a spaced-apart facing relationship with the first electrode surface; and, a third electrode surface and a fourth electrode surface, the fourth electrode surface disposed in a spaced-apart facing relationship with the third electrode surface; and, at least an electrical controller in communication with the analyzer assembly for establishing a first electric field within the analytical gap for separating ions according to the FAIMS principle when operating in the first operating mode and for establishing a second electrical field within the analytical gap for transmitting ions without separation according to the FAIMS principle when operating in the second operating mode, wherein each of the at least four electrode surfaces is aligned toward the longitudinal axis of the analytical gap.

According to another aspect of the instant invention, provided is an apparatus for transmitting ions in the gas phase, the apparatus selectably switchable between a first operating mode for transmitting ions with separation according to the FAIMS principle and a second operating mode for transmitting ions using the principle of an rf-only ion guide device, the apparatus comprising: an analyzer assembly comprising an analytical gap defined by a space that is bounded by at least four flat-plate electrodes, the at least four flat-plate electrodes arranged around a longitudinal axis that extends along a first direction through the analytical gap, the at least four flat-plate electrodes comprising: a first flat-plate electrode and a second flat-plate electrode, the second flat-plate electrode facing the first flat-plate electrode and spaced-apart therefrom along a second direction that is normal to the first direction; and, a third flat-plate electrode and a fourth flat-plate electrode, the fourth flat-plate electrode facing the third flat-plate electrode and spaced-apart therefrom along a third direction that is substantially normal to both the first direction and the second direction; a plurality of lateral segment electrodes, including a first lateral segment electrode and a second lateral segment electrode disposed one each adjacent opposite edges of the first flat-plate electrode and extending along the first direction, and a third lateral segment electrode and a fourth lateral segment electrode disposed one each adjacent opposite edges of the second flat-plate electrode and extending along the first direction; and, at least an electrical controller in communication with the analyzer assembly for establishing a first electric field within the analytical gap for separating ions according to the FAIMS principle when operating in the first operating mode and for establishing a second electrical field within the analytical gap for transmitting ions without separation according to the FAIMS principle when operating in the second operating mode.

BRIEF DESCRIPTION OF THE DRAWINGS

Exemplary embodiments of the invention will now be described in conjunction with the following drawings, in which similar reference numerals designate similar items.

DESCRIPTION OF EMBODIMENTS OF THE INSTANT INVENTION

The following description is presented to enable a person skilled in the art to make and use the invention, and is provided in the context of a particular application and its requirements. Various modifications to the disclosed embodiments will be readily apparent to those skilled in the art, and the general principles defined herein may be applied to other embodiments and applications without departing from the spirit and the scope of the invention. Thus, the present invention is not intended to be limited to the embodiments disclosed, but is to be accorded the widest scope consistent with the principles and features disclosed herein.

Figure 1:
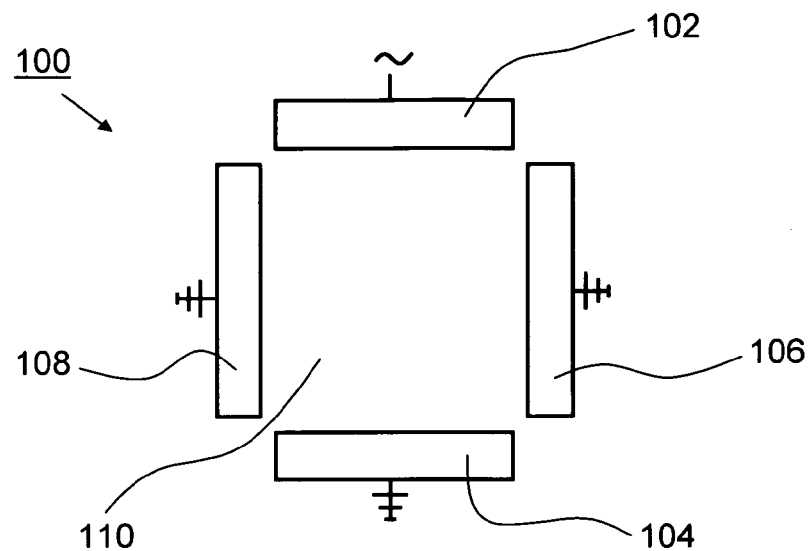
FIG. 1 is an end view of a FAIMS apparatus according to an embodiment of the instant invention.

Referring to FIG. 1, shown is an end view of a FAIMS apparatus according to an embodiment of the instant invention. The FAIMS apparatus, shown generally at 100, includes a quadrupole assembly of flat-plate electrodes 102, 104, 106 and 108. An analyzer region 110 is defined within the space that is bounded by facing electrodes 102 and 104, and by facing electrodes 106 and 108. In FIG. 1, the flat-plate electrodes 102, 104, 106 and 108 are arranged symmetrically about a longitudinal axis of the FAIMS apparatus extending along a first direction that is perpendicular to the plane of the page. The electrodes 102 and 104 are spaced one from the other along a second direction that is normal to the first direction, and the electrodes 106 and 108 are similarly spaced apart along a third direction that is normal to both the first direction and the second direction. Accordingly, flat-plate electrodes 102, 104, 106 and 108 define a square in a cross section taken in a plane normal to the longitudinal axis. The flat-plate electrodes are embedded in a not illustrated electrically insulating material, such as for instance PEEK™, and the entire electrode assembly is supported within a housing including inlets and outlets for providing a flow of carrier gas through the analyzer region 110. Electrical contacts are provided on at least some of the electrodes for coupling to an electrical controller 112 and for receiving various potentials therefrom. Optionally, a temperature controller is provided for controllably affecting the temperature of the gas between the electrodes 102, 104, 106 and 108, and/or for establishing temperature gradients within the gas between the electrodes 102, 104, 106 and 108. The effect of temperature gradients is discussed in greater detail, in the following sections.

By the application of appropriate voltages to the flat-plate electrodes 102, 104, 106 and 108 using electrical controller 112, the analyzer region 110 is selectably operable in an rf-only mode or in FAIMS mode. FIG. 1 illustrates application of a radio frequency asymmetric waveform potential to electrode 102, with the remaining electrodes 104, 106 and 108 at ground potential. Application of potentials as illustrated in FIG. 1 results in FAIMS mode operation. Note that FAIMS is operable over a wide range of pressure values, from greater than atmospheric pressure down to the millitorr range. Ions are separated in FAIMS on the basis of the compound dependent behavior of KH, the high field mobility constant, as a function of the applied electric field strength. It is to be understood that the strength of the field is actually E/N where E is the field in volts/cm and N is the number density of the bath gas. Clearly, the application of lower voltages is appropriate under conditions of lower gas pressure while higher voltages are required at higher gas pressure, in each case arriving at the same E/N. The behavior of ions in the FAIMS technology is based on changes in the mobility of the ion under conditions of changing E/N, which is often simplified to "conditions of changing electric field strength."

Because the asymmetric waveform is applied between flat-plate electrodes 102 and 104, the ion separation resolution is very high in the device that is shown in FIG. 1 but ion focusing does not occur under normal operating conditions. Accordingly, ion transmission efficiency suffers when the DV is applied since ions are lost to the electrode surfaces due to diffusion and space-charge repulsion effects. The ion focusing effect in FAIMS requires an electric field E/N that varies in strength over a distance, as is produced using curved electrode surfaces, such as for instance concentric cylinders, spheres, curved plates, etc. Another way to produce an electric field E/N that varies in strength over a distance is by establishing a temperature gradient in the gas between the electrodes, as is described by Guevremont et al. in U.S. patent application Ser. No. 11/038,166 filed on Jan. 21, 2005, the entire contents of which is incorporated herein by reference. Optionally, additional potentials may be applied to facing electrodes 106 and 108, as is described in greater detail with reference to FIG. 6, in order to prevent ions from spreading out along the third direction within analyzer region 110.

Application of a radio frequency (rf) waveform (which may take the form of a sinusoidal waveform) to opposed pairs of the flat-plate electrodes 102, 104, 106 and 108 in a prescribed phase relationship (e.g., 180 degrees out of phase for the four-electrode structure depicted herein) in the absence of the above-described asymmetric waveform results in rf-only mode operation. In this mode a wide range of ions are transmitted simultaneously through the analyzer region 110. The term "rf-only mode" is used herein to denote an operating mode in which ions having a relatively broad (as compared to operation in the FAIMS mode) range of mass-to-charge ratios (m/z's) are transported through the quadrupole assembly, and does not exclude the inclusion of a DC component in the waveforms applied to the electrodes in order to, for example, provide some rough filtering of ions above or below an m/z range of interest. When a bath gas is present, collisional cooling of the ions occurs such that the ions migrate toward the central longitudinal axis of the analyzer region 110. As a result, very high ion transmission efficiency may be achieved when operating in the rf-only mode. Accordingly, the FAIMS apparatus shown in FIG. 1 supports electronic removal of FAIMS from a system when the FAIMS separation is not required, and further supports high ion transmission efficiency in both the FAIMS and rf-only operating modes.

Figure 2:
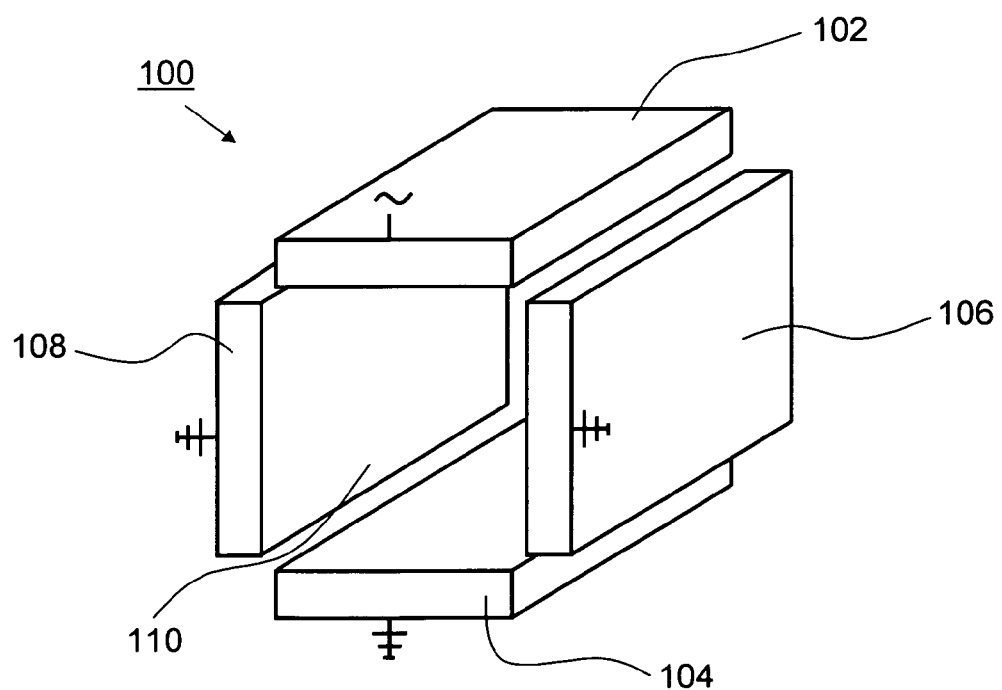
FIG. 2 is a perspective view of the FAIMS apparatus shown in FIG. 1.

Referring now to FIG. 2, shown is a perspective view of the FAIMS apparatus of FIG. 1. The electrodes 102, 104, 106 and 108 are provided optionally as flat-plates or as thin ribbons that may be stretched to give a very precise flat surface. The length of the electrodes 102, 104, 106 and 108 are equal, with typical values for length being in the range 0.5-5 cm. In the device that is shown in FIG. 2, the widths of the electrodes 102, 104, 106 and 108 also are equal, with typical values for width being in the range 3-10 mm.

Figure 3:
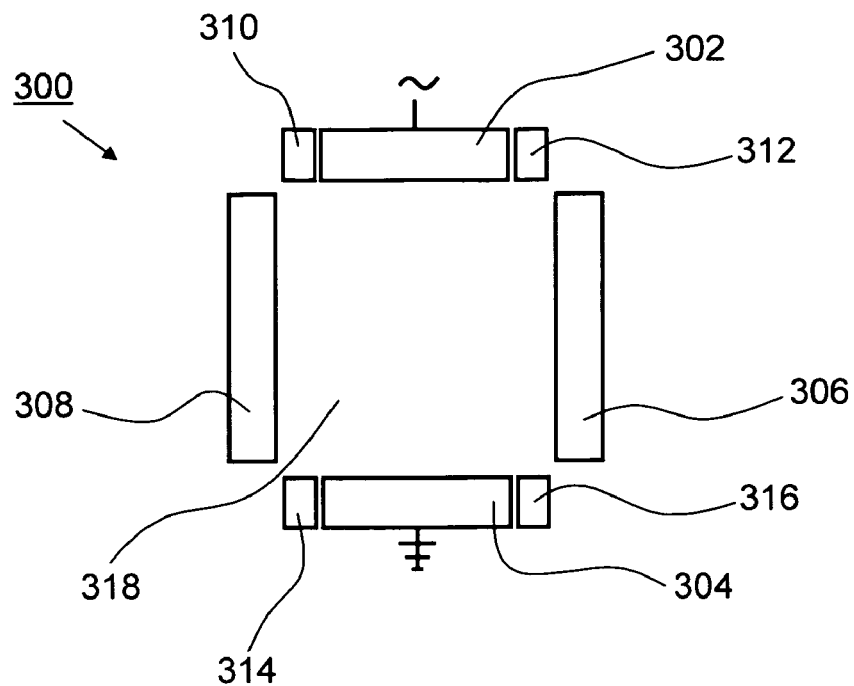
FIG. 3 is an end view of a FAIMS apparatus including lateral segment electrodes, according to an embodiment of the instant invention.
Figure 4:
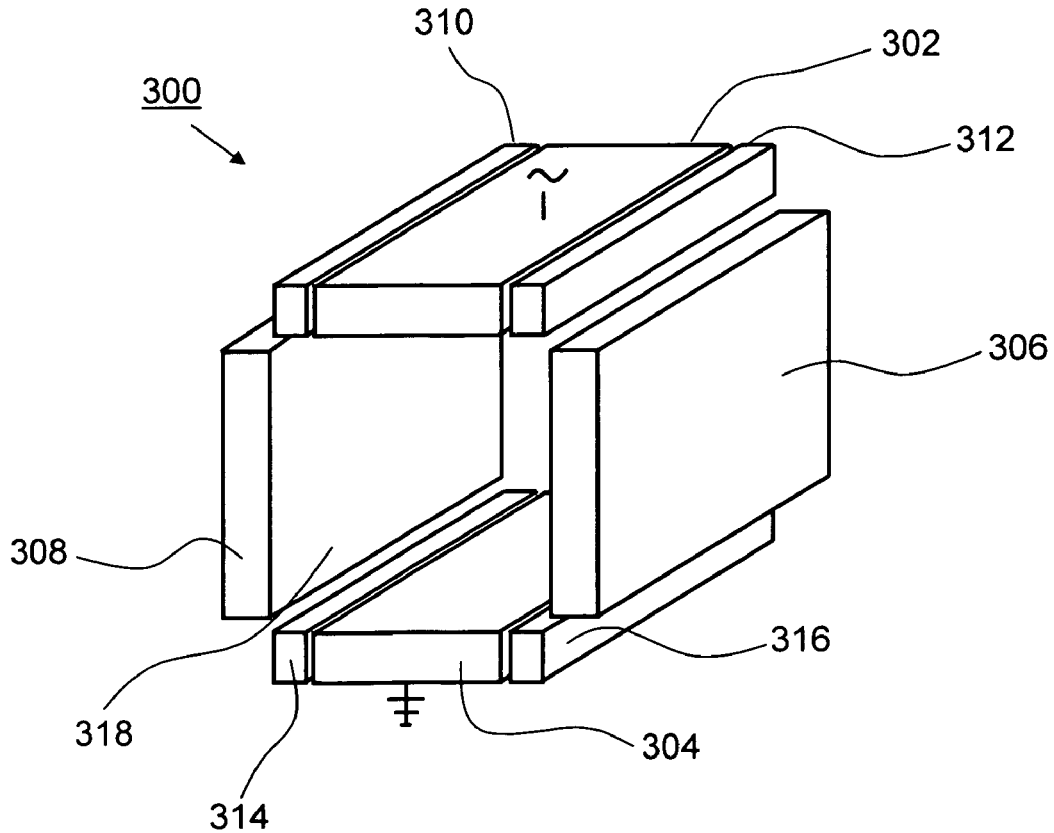
FIG. 4 is a perspective view of the FAIMS apparatus shown in FIG. 2.

FIG. 3 is an end view of a FAIMS apparatus including lateral segment electrodes, according to an embodiment of the instant invention. The FAIMS apparatus, shown generally at 300, includes a quadrupole assembly of flat-plate electrodes 302, 304, 306 and 308. In addition, lateral segment electrodes 310 and 312 are disposed one each adjacent opposite edges of flat-plate electrode 302, and lateral segment electrodes 314 and 316 are disposed one each adjacent opposite edges of flat-plate electrode 304. Referring also to FIG. 4, the lateral segment electrodes 310, 312, 314 and 316 extend along the length of the FAIMS apparatus 300. The flat-plate electrodes 302, 304, 306 and 308 are arranged about a longitudinal axis of the FAIMS apparatus extending along a first direction that is perpendicular to the plane of the page in FIG. 3. The electrodes 302 and 304 are spaced one from the other along a second direction that is normal to the first direction, and the electrodes 306 and 308 are similarly spaced apart along a third direction that is substantially normal to both the first direction and the second direction. Accordingly, flat-plate electrodes 302, 304, 306 and 308, together with the lateral segment electrodes 310, 312, 314 and 316, define generally a square in a cross section taken in a plane normal to the longitudinal axis. The flat-plate electrodes and the lateral segment electrodes are embedded in a not illustrated electrically insulating material, such as for instance PEEK™, and the entire electrode assembly is supported within a housing including inlets and outlets for providing a flow of carrier gas through the analyzer region 318. Electrical contacts are provided on at least some of the electrodes for coupling to an electrical controller 320 and for receiving various potentials therefrom. Optionally, a temperature controller is provided for controllably affecting the temperature of the gas between the electrodes 302, 304, 306 and 308, and/or for establishing temperature gradients within the gas between the electrodes 302, 304, 306 and 308.

By the application of appropriate voltages to the flat-plate electrodes 302, 304, 306 and 308 using electrical controller 320, the analyzer region 318 is selectably operable in an rf-only mode or in FAIMS mode. In addition, each of the lateral segment electrodes 310, 312, 314 and 316 includes an electrical contact for receiving potentials from the electrical controller 320. Application of predetermined potentials to the lateral segment electrodes 310, 312, 314 and 316 results in the generation of DC fields within the analyzer region 318 that laterally (in the dimension transverse to the primary direction of ion travel and orthogonal to the dimension of ion separation extending between electrodes 302 and 304) focus the ions towards the center of the device in order to minimize losses due to ion discharge on electrodes 306 and 308 when operating in FAIMS mode, and can be used to accelerate the ions in a transmission mode. For example, when operated in FAIMS mode, electrode 304 may be maintained at ground, segment electrodes 310, 312, 314, and 316 could all be at +10 V (for positive ions), and electrodes 306 and 308 could be at +25 V. When operation in rf-only (transmission) mode is desired, segment electrodes 310, 312, 314 and 316 are maintained at the same DC voltage to produce a balanced field at the centerline, and the flat-plate electrodes have an rf waveform (optionally including a DC component) applied thereto in the prescribed phase relationship. Optionally, the lateral segment electrodes 310, 312, 314 and 316 are segmented along the length of the device, for establishing desired DC potential gradients along the length of the device to facilitate ion transport. In general, the spacing between adjacent segments should be kept small, typical values being in the range 1-2 mm. In an alternative operating mode for FAIMS separation, the asymmetric waveform is applied to electrode 302 and to segment electrodes 310 and 312. The DC offset (e.g., +10 V) is still applied to segment electrodes 310, 312, 314, and 316. In this alternative mode, the CV is the same between electrodes 302 and 304, between electrodes 312 and 316, and between electrodes 310 and 314. Further optionally, each one of the segment electrodes 310, 312, 314, and 316 is further segmented, and DC potentials are applied in small increments that increase in magnitude moving out away from the center of the device. Application of the asymmetric waveform to electrode 302 and to segment electrodes 310 and 312 reduces the possibility of electrical discharge.

Again, it should be noted that FAIMS is operable over a wide range of pressure values, from greater than atmospheric pressure down to the millitorr range. Ions are separated in FAIMS on the basis of the compound dependent behavior of KH, the high field mobility constant, as a function of the applied electric field strength. It is to be understood that the strength of the field is actually E/N where E is the field in volts/cm and N is the number density of the bath gas. Clearly, the application of lower voltages is appropriate under conditions of lower gas pressure while higher voltages are required at higher gas pressure, in each case arriving at the same E/N. The behavior of ions in the FAIMS technology is based on changes in the mobility of the ion under conditions of changing E/N, which is often simplified to "conditions of changing electric field strength."

Because the asymmetric waveform is applied between flat-plate electrodes 302 and 304, the ion separation resolution can be very high in the device that is shown in FIG. 3 but ion focusing does not occur under normal operating conditions. Accordingly, ion transmission efficiency suffers when the DV is applied since ions are lost to the electrode surfaces due to diffusion and space-charge repulsion effects. The ion focusing effect in FAIMS requires an electric field E/N that varies in strength over a distance, as is produced using curved electrode surfaces such as for instance concentric cylinders, spheres, curved plates, etc. Another way to produce an electric field E/N that varies in strength over a distance is by establishing a temperature gradient in the gas between the electrodes. Furthermore, as described above, focusing fields may be established within the analyzer region 318 by the application of predetermined potentials to the lateral segment electrodes 310, 312, 314, and 316. Optionally, additional potentials may be applied to facing electrodes 306 and 308 in order to prevent ions from spreading out along the third direction within analyzer region 310.

Application of only a radio frequency (rf) waveform to the flat-plate electrodes 302, 304, 306 and 308 results in rf-only mode operation. In this mode a wide range of ions are transmitted simultaneously through the analyzer region 310. When a bath gas is present, collisional cooling of the ions occurs such that the ions migrate toward the longitudinal axis of the analyzer region 310. As a result, very high ion transmission efficiency is achieved when operating in the rf-only mode. Accordingly, the FAIMS apparatus shown in FIG. 3 supports electronic removal of FAIMS from a system when the FAIMS separation is not required, and further supports high ion transmission efficiency in both the FAIMS and rf-only operating modes.

Figure 5:
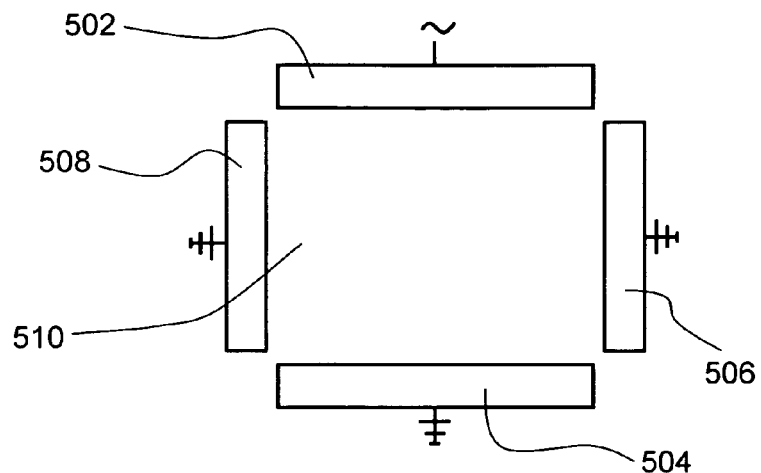
FIG. 5 is an end view of another FAIMS apparatus according to an embodiment of the instant invention.

FIG. 5 is an end view of another FAIMS apparatus according to an embodiment of the instant invention. The FAIMS apparatus shown in FIG. 5 includes a quadrupole assembly of flat-plate electrodes 502, 504, 506 and 508. An analyzer region 510 is defined within the space that is bounded by facing electrodes 502 and 504, and by facing electrodes 506 and 508. In FIG. 5, the flat-plate electrodes 502, 504, 506 and 508 are arranged symmetrically about a longitudinal axis of the FAIMS apparatus extending along a first direction that is perpendicular to the plane of the page. The electrodes 502 and 504 are spaced one from the other along a second direction that is normal to the first direction. In this case, the width of electrodes 506 and 508 is narrower than the width of electrodes 502 and 504. Accordingly, the spacing between electrodes 506 and 508 along a third direction that is normal to both the first direction and the second direction is smaller than the spacing between electrodes 502 and 504 along the second direction. Accordingly, flat-plate electrodes 502, 504, 506 and 508 define a non-equilateral rectangle in a cross section taken in a plane normal to the longitudinal axis. The dimensions of the rectangular in cross section analyzer region 510 are selected to optimize field lines resulting from application of the asymmetric waveform potential and compensation voltage.

Referring still to FIG. 5, the flat-plate electrodes 502, 504, 506 and 508 are embedded in a not illustrated electrically insulating material, such as for instance PEEK™, and the entire electrode assembly is supported within a housing including inlets and outlets for providing a flow of carrier gas through the analyzer region 510. Electrical contacts are provided on at least some of the electrodes for coupling to an electrical controller 512 and for receiving various potentials therefrom. Optionally, a temperature controller is provided for controllably affecting the temperature of the gas between the electrodes 502, 504, 506 and 508, and/or for establishing temperature gradients within the gas between the electrodes 502, 504, 506 and 508.

By the application of appropriate voltages to the flat-plate electrodes 502, 504, 506 and 508 using electrical controller 512, the analyzer region 510 is selectably operable in an rf-only mode or in FAIMS mode. FIG. 5 illustrates application of a radio frequency asymmetric waveform potential to electrode 502, with the remaining electrodes 504, 506 and 508 at ground potential. Application of potentials as illustrated in FIG. 5 results in FAIMS mode operation.

Again, it should be noted that FAIMS is operable over a wide range of pressure values, from greater than atmospheric pressure down to the millitorr range. Ions are separated in FAIMS on the basis of the compound dependent behavior of KH, the high field mobility constant, as a function of the applied electric field strength. It is to be understood that the strength of the field is actually E/N where E is the field in volts/cm and N is the number density of the bath gas. Clearly, the application of lower voltages is appropriate under conditions of lower gas pressure while higher voltages are required at higher gas pressure, in each case arriving at the same E/N. The behavior of ions in the FAIMS technology is based on changes in the mobility of the ion under conditions of changing E/N, which is often simplified to "conditions of changing electric field strength."

Because the asymmetric waveform is applied between flat-plate electrodes 502 and 504, the ion separation resolution can be very high in the device that is shown in FIG. 5 but ion focusing does not occur under normal operating conditions. Accordingly, ion transmission efficiency suffers when the DV is applied since ions are lost to the electrode surfaces due to diffusion and space-charge repulsion effects. The ion focusing effect in FAIMS requires an electric field E/N that varies in strength over a distance, as is produced using curved electrode surfaces such as for instance concentric cylinders, spheres, curved plates, etc. As described above, another way to produce an electric field E/N that varies in strength over a distance is by establishing a temperature gradient in the gas between the electrodes. Optionally, additional potentials (e.g. rf and DC) may be applied to facing electrodes 506 and 508 in order to prevent ions from spreading out along the third direction within analyzer region 510.

Application of only a radio frequency (rf) (e.g., sinusoidal) waveform to the flat-plate electrodes 502, 504, 506 and 508 results in rf-only mode operation. In this mode a wide range of ions are transmitted simultaneously through the analyzer region 510. When a bath gas is present, collisional cooling of the ions occurs such that the ions migrate toward the longitudinal axis of the analyzer region 510. As a result, very high ion transmission efficiency is achieved when operating in the rf-only mode. Accordingly, the FAIMS apparatus shown in FIG. 5 supports electronic removal of FAIMS from a system when the FAIMS separation is not required, and further supports high ion transmission efficiency in both the FAIMS and rf-only operating modes.

Figure 6:
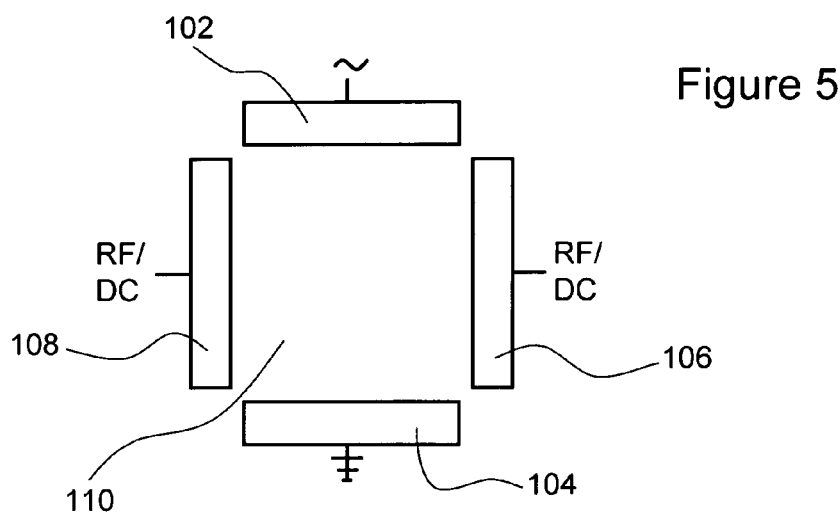
FIG. 6 is an end view of the FAIMS apparatus of FIG. 1, showing a first alternate scheme for applying potentials between the electrodes.

FIG. 6 is an end view of the FAIMS apparatus of FIG. 1, showing a first alternate scheme for applying potentials between the electrodes. FIG. 6 shows a specific example of operation in FAIMS mode with an asymmetric waveform potential applied to flat-plate electrode 102, the facing electrode 104 held at ground potential, and a focusing potential applied to flat-plate electrodes 106 and 108.

Figure 7:
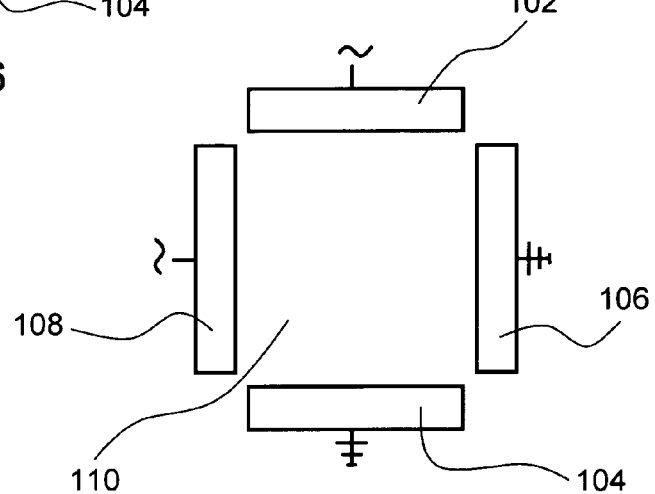
FIG. 7 is an end view of the FAIMS apparatus of FIG. 1, showing a second alternate scheme for applying potentials between the electrodes.

FIG. 7 is an end view of the FAIMS apparatus of FIG. 1, showing a second alternate scheme for applying potentials between the electrodes. In FIG. 7, the asymmetric waveform is applied to adjacent flat-plate electrodes 102 and 108, while the remaining flat-plate electrodes 104 and 106 are held at ground potential.

Figure 8:
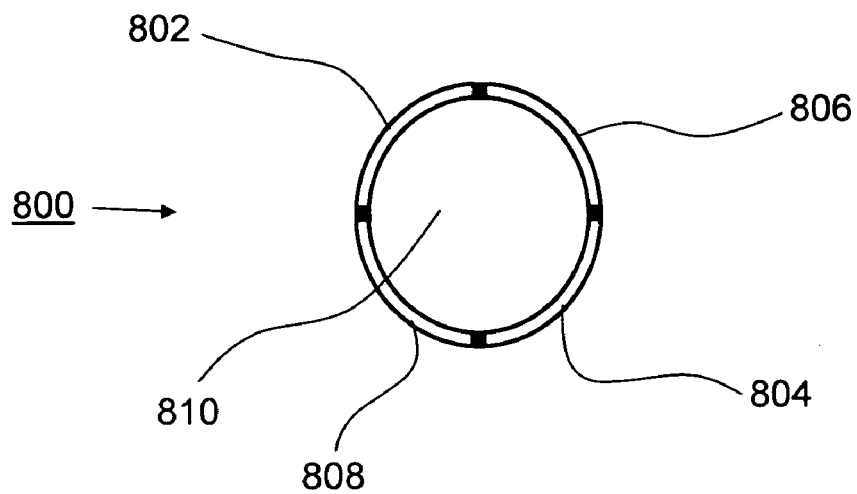
FIG. 8 is an end view of another FAIMS apparatus according to an embodiment of the instant invention; and, FIG. 9 is a schematic illustration showing a triple quadrupole mass spectrometer including a FAIMS apparatus according to an embodiment of the instant invention.

FIG. 8 is an end view of another FAIMS apparatus according to an embodiment of the instant invention. The FAIMS apparatus, shown generally at 800, includes a quadrupole assembly of electrode segments 802, 804, 806 and 808 that are curved concavely toward a longitudinal axis perpendicular to the plane of the page. An analyzer region 810 is defined within the space that is bounded by facing electrode segments 802 and 804, and by facing electrode segments 806 and 808. The electrode segments are separated by electrically insulating material. Optionally, the electrode segments are formed as discrete metallized portions of the inner surface of an electrically insulating support, such as for instance a precision bore quartz tube. The entire electrode assembly is supported within a housing including inlets and outlets for providing a flow of carrier gas through the analyzer region 810. The cylindrical shape of the FAIMS apparatus 800 contains the flow of carrier gas. Electrical contacts (not shown) are also provided on at least some of the electrodes for coupling to a not illustrated electrical controller and for receiving various potentials therefrom. Optionally, a temperature controller is provided for controllably affecting the temperature of the gas between the electrodes 802, 804, 806 and 808, and/or for establishing temperature gradients within the gas between the electrodes 802, 804, 806 and 808.

By the application of appropriate voltages to the electrode segments 802, 804, 806 and 808 using a not illustrated electrical controller, the analyzer region 810 is selectably operable in an rf-only mode or in FAIMS mode.

Figure 9:
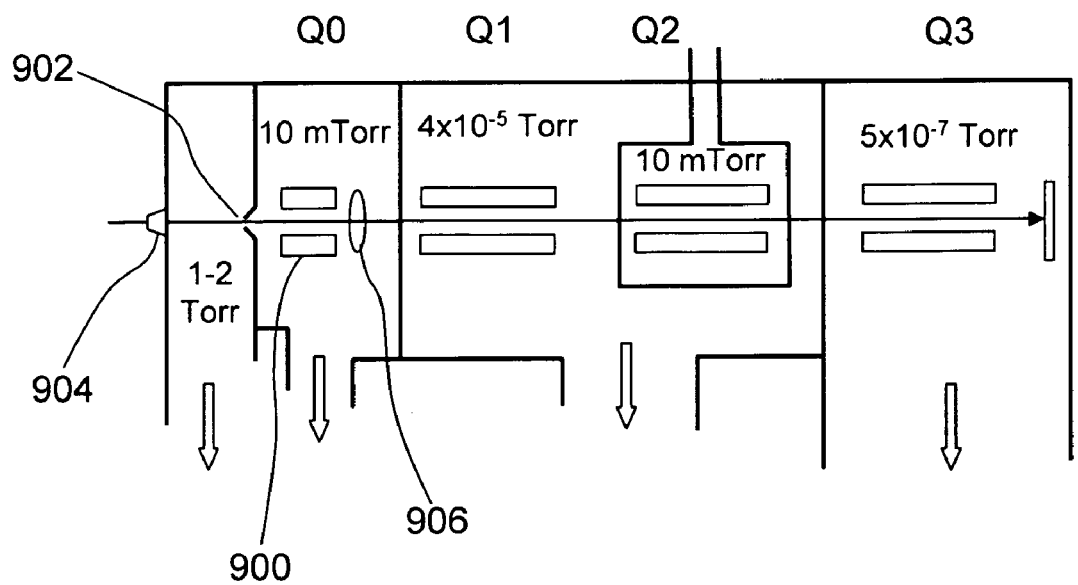

FIG. 9 is a schematic illustration showing a triple quadrupole mass spectrometer including a FAIMS/rf-only apparatus according to an embodiment of the instant invention. In this particular example, the FAIMS/rf-only apparatus 900 according to an embodiment of the instant invention is disposed immediately behind the entrance orifice 902 of a triple quadrupole mass spectrometer. In this region, Q0, the operating pressure is approximately 10 mTorr. Ions produced in a high-pressure electrospray or APCI ion source 904 pass through the entrance orifice 902 and enter the FAIMS/rf-only apparatus 900. When FAIMS separation is desired, the appropriate combination of asymmetric waveform potential and DC compensation voltage are applied to the electrodes and the ions are separated via the FAIMS mechanism. Alternatively, the apparatus 902 is operated in rf-only mode when FAIMS separation is not required. Accordingly, the FAIMS/rf-only apparatus is selectably operated in FAIMS mode and rf-only mode, during different periods of time, without requiring physical removal of any components of the system. Also shown in FIG. 9 is a lens 906 disposed after the FAIMS/rf-only apparatus 900 for focusing ions into the first quadrupole mass filter Q1 and subsequent regions of the mass spectrometer.

The embodiments of the instant invention have been described by way of a specific and non-limiting example in which four electrodes, arranged in opposite pairs in quadrupole geometry, define the analyzer region. It is to be understood that the general principles outlined supra may be applied to other multipole structures having opposed electrode pairs, such as for instance 6- or 8-electrode structures.

Numerous other embodiments may be envisaged without departing from the spirit and scope of the invention.

What is claimed is:

1. An apparatus for transmitting ions in the gas phase, the apparatus selectably switchable between a first operating mode for transmitting ions with separation according to the FAIMS principle and a second operating mode for transmitting ions using the principle of an rf-only ion guide device, the apparatus comprising:

an analyzer assembly comprising an analytical gap defined by a space that is bounded by at least four flat-plate electrodes, the at least four flat-plate electrodes arranged around a longitudinal axis that extends along a first direction through the analytical gap, the at least four flat-plate electrodes comprising:

a first flat-plate electrode and a second flat-plate electrode, the second flat-plate electrode facing the first flat-plate electrode and spaced-apart therefrom along a second direction that is normal to the first direction; and, a third flat-plate electrode and a fourth flat-plate electrode, the fourth flat-plate electrode facing the third flat-plate electrode and spaced-apart therefrom along a third direction that is substantially normal to both the first direction and the second direction;

a plurality of lateral segment electrodes, including a first lateral segment electrode and a second lateral segment electrode disposed one each laterally adjacent opposite edges of the first flat-plate electrode and extending along the first direction, and a third lateral segment electrode and a fourth lateral segment electrode disposed one each laterally adjacent opposite edges of the second flat-plate electrode and extending along the first direction; and, at least an electrical controller in communication with the analyzer assembly for establishing a first electric field within the analytical gap for separating ions according to the FAIMS principle when operating in the first operating mode and for establishing a second electrical field within the analytical gap for transmitting ions using the principle of an rf-only ion guide device when operating in the second operating mode, the electrical controller being further configured to apply DC potentials to the plurality of lateral segment electrodes to generate a DC field that laterally focuses ions to the longitudinal axis.

2. An apparatus according to claim 1, wherein a width of the first and second electrodes measured along the third direction is smaller than a width of the third and fourth electrodes measured along the second direction.

3. An apparatus according to claim 1, wherein the analyzer assembly comprises a housing for containing the first flat-plate electrode, the second flat-plate electrode, the third flat-plate electrode and the fourth flat-plate electrode.

4. An apparatus according to claim 3, wherein the analyzer assembly comprises a support member fabricated from an electrically insulating material, for supporting the first flat-plate electrode, the second flat-plate electrode, the third flat-plate electrode and the fourth flat-plate electrode within the housing, and for electrically insulating the first flat-plate electrode, the second flat-plate electrode, the third flat-plate electrode and the fourth flat-plate electrode one from the other.

5. An apparatus according to claim 1, comprising an ion focusing lens disposed after the analytical gap for focusing ions for introduction into an inlet orifice of a mass spectrometer.

6. An apparatus according to claim 1, wherein the at least an electrical controller comprises a radio-frequency asymmetric waveform (DV) potential source and a direct current compensation (CV) potential source, for providing a predetermined combination of DV and CV potentials for establishing the first electrical field within the analytical gap when operating in the first operating mode.

7. An apparatus according to claim 6, wherein the at least an electrical controller comprises a symmetric alternating current (AC) potential source and a direct current (DC) potential source, for providing a predetermined combination of AC and DC potentials for establishing the second electrical field within the analytical gap when operating in the second operating mode.

8. An apparatus according to claim 7, wherein the at least an electrical controller comprises a plurality of separate electrical controllers.

9. An apparatus according to claim 7, wherein the CV potential source and the DC potential source are a same potential source.

10. An apparatus according to claim 1, wherein each of the plurality of lateral segment electrodes is longitudinally segmented into sections, and wherein the electrical controller is configured to apply different potentials to each of the segments to generate a DC potential gradient along the longitudinal axis.

* * * * *